US00PP22404P3

(12) United States Plant Patent
Zaiger et al.

(10) Patent No.: US PP22,404 P3
(45) Date of Patent: Dec. 27, 2011

(54) PEACH TREE NAMED 'SAUZEE LADY'

(50) Latin Name: *Prunus persica*
Varietal Denomination: Sauzee Lady

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 477 days.

(21) Appl. No.: 12/384,678

(22) Filed: Apr. 8, 2009

(65) Prior Publication Data

US 2010/0293672 P1 Nov. 18, 2010

(51) Int. Cl.
*A01H 5/00* (2006.01)

(52) U.S. Cl. ..... Plt./194

(58) Field of Classification Search ..... Plt./194
See application file for complete search history.

(56) References Cited

U.S. PATENT DOCUMENTS

| | | | | | |
|---|---|---|---|---|---|
| PP621 | P | * | 3/1944 | Lammerts | Plt./196 |
| PP1,060 | P | * | 1/1952 | Anderson | Plt./190 |
| PP2,663 | P | * | 8/1966 | Zaiger | Plt./198 |
| PP2,794 | P | * | 2/1968 | Anderson | Plt./192 |
| PP7,532 | P | * | 5/1991 | Zaiger et al. | Plt./196 |
| PP16,179 | P3 | * | 1/2006 | Zaiger et al. | Plt./197 |
| PP20,639 | P2 | * | 1/2010 | Zaiger et al. | Plt./198 |

* cited by examiner

*Primary Examiner* — Wendy C Haas

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous upright growth of tree.
2. Producing peento shaped fruit.
3. Fruit with firm, white flesh, good flavor and eating quality.
4. Fruit with an attractive light red blush.
5. Regular and productive bearer of medium to large sized fruit.

1 Drawing Sheet

Botanical designation: *Prunus persica.*
Variety denomination: 'Sauzee Lady'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peach and nectarine trees, which are known to us, and mentioned herein, 'Sugar Lady' Peach (U.S. Plant Pat. No. 7,532), 'Carolyn' Peach (non-patented), 'Fayette' Peach (non-patented), 'May Grand' Nectarine (U.S. Plant Pat. No. 2,794), 'Royal Gold' Peach (U.S. Plant Pat. No. 2,663), 'Red Grand' Nectarine (U.S. Plant Pat. No. 1,060) 'Redwing' Peach (U.S. Plant Pat. No. 621) 'Sauzee Queen' Peach (U.S. Plant Pat. No. 16,179) and the proprietary selections '52LA314' and '333LH428'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was originated by us in our experimental orchard located near Modesto, Stanislaus County, Calif. as a first generation cross between two proprietary seedlings with the field identification numbers '52LA314' and '333LH428'. The seed parent (52LA314) originated from crosses between the following varieties; 'Fayette' Peach (non-patented), 'Royal Gold' Peach (U.S. Plant Pat. No. 2,663), 'Redwing' Peach (U.S. Plant Pat. No. 621), 'Sugar Lady' Peach (U.S. Plant Pat. No. 7,532) and 'Red Grand' Nectarine (U.S. Plant Pat. No. 1,060). The pollen parent (333LH428) originated from crosses between the following varieties; 'Carolyn' Peach (non-patented), 'Fayette' Peach (non-patented), 'May Grand' Nectarine (U.S. Plant Pat. No. 2,794) and a peento peach of unknown parentage. We planted and grew a large number of seed from this first generation cross on their own root system, and under careful and close observation, recognized the desirable tree and peento fruit characteristics of the present variety and selected it for asexual propagation and commercialization in 2001.

ASEXUAL REPRODUCTION OF THE VARIETY

Asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of peach tree (*Prunus persica*) is of large size, vigorous upright growth, a regular and productive bearer of medium to large, white flesh clingstone fruit. The fruit is further characterized by having an attractive light red blush, mild, sweet sub-acid flavor, very good eating quality and is peento in shape. In comparison to its proprietary seed parent (52LA314) the new variety is a peach instead of a nectarine tree, the fruit is peento in shape compared to globose and is approximately 1 month earlier in maturity. In comparison to its proprietary pollen parent (333LH428) the fruit has firmer texture, more uniform attractive light red skin color, is larger in size with the same peento shape and requires approximately 300 more winter chilling hours at or below 45° F. In comparison to the commercial variety 'Sauzee Queen' Peach (U.S. Plant Pat. No. 16,179) the fruit of the new variety matures approximately 73 days later.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 7 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 7 year old specimens grown near Modesto, Calif., with color in accordance with Munsell Book of Color.

Tree:

- *Size.*—Large. Pruned to 3 to 3.5 meters in height for economical harvesting of fruit. Average spread 3 to 3.5 meters, varies with different cultural practices.
- *Vigor.*—Vigorous, growth of 1.5 to 2 meters the first growing season, varies with soil type, fertility and cultural practices.
- *Form.*—Upright, usually pruned to vase shape.
- *Branching habit.*—Upright, crotch angle approximately 35°, increases with heavy crop load.
- *Productivity.*—Productive, thinning and spacing necessary for desired marketable size fruit. Number of fruit set varies with climatic conditions during blooming period.
- *Bearer.*—Regular, has had adequate fruit set 5 consecutive years. No alternate bearing observed.
- *Fertility.*—Self-fertile.
- *Density.*—Medium dense. Pruning to vase shape desirable for sunlight penetration to enhance fruit color and health of fruit wood.
- *Hardiness.*—Hardy in all stone fruit growing areas of California. Tree grown in USDA Hardiness Zone 9. Winter chilling requirement approximately 800 hours at or below 45° F.

Trunk:

- *Size.*—Medium. Average circumference 52.1 cm at 17.8 cm above ground on a 7 year old tree.
- *Stocky.*—Medium stocky.
- *Texture.*—Medium rough, becoming rougher with age.
- *Color.*—Varies from 10YR 3/2 to 2.5Y 5/2.

Branches:

- *Size.*—Medium. Average circumference 15.5 cm at 1.1 meters above ground.
- *Surface texture.*—New growth relatively smooth. Mature growth medium rough, roughness increases with age.
- *Lenticels.*—Average number 23 in a 25.8 sq cm section. Average length 3.6 mm. Average width 2.1 mm. Color varies from 7.5YR 7/8 to 7.5YR 6/10.
- *Color.*—New growth varies from 2.5GY 6/6 to 5GY 6/6. Mature growth varies from 10YR 3/4 to 2.5Y 3/4, varies with age of growth.

Leaves:

- *Size.*—Large. Average length 140.8 mm. Average width 41.6 mm.
- *Form.*—Lanceolate.
- *Apex.*—Acuminate.
- *Base.*—Cuneate.
- *Margin.*—Crenate.
- *Thickness.*—Medium.
- *Surface texture.*—Upper surface relatively smooth, slight indentation over midrib and leaf veins. Lower surface relatively smooth, small ridges created by midrib and pinnate venation. Both surfaces glabrous.
- *Stipules.*—None observed on mature leaves.
- *Petiole.*—Average length 11.3 mm. Average width 1.7 mm. Longitudinally grooved. Surface glabrous. Color varies from 2.5GY 7/6 to 2.5GY 6/6.
- *Glands.*—Reniform. Size — small to medium. Average length 0.9 mm. Average diameter 0.7 mm. Average number 4, varies from 1 to 6. Located on base of leaf blade and upper portion of the petiole. Color varies from 2.5GY 7/8 to 2.5GY 6/6.
- *Color.*—Upper surface varies from 5GY 4/6 to 5GY 3/6. Lower surface varies from 5GY 5/4 to 5GY 4/4. Midvein color varies from 2.5GY 8/4 to 2.5GY 7/6.

Flower buds:

- *Size.*—Large. Average length 16.6 mm. Average diameter 9.8 mm.
- *Hardiness.*—Hardy with respect to California winters.
- *Form.*—Conical, becoming elongated before opening.
- *Pedicel.*—Average length 3.6 mm. Average width 0.9 mm. Color varies from 2.5GY 6/6 to 5GY 6/8.
- *Color.*—Varies from 7.5RP 6/10 to 5RP 8/6.

Flowers:

- *Blooming period.*—Date of First Bloom Mar. 2, 2008. Date of Petal Fall Mar. 12, 2008, varies slightly with climatic conditions.
- *Size.*—Large, showy. Average height 20.0 mm. Average diameter 48.4 mm.
- *Petals.*—Number 5, alternately arranged to sepals. Size — large. Average length 20.0 mm. Average width 19.0 mm. Form — orbicular, narrows at point of attachment. Margin sinuate. Both upper and lower surfaces glabrous. Color varies from 5RP 9/2 to 7.5RP 8/4.
- *Sepals.*—Number 5, alternately arranged to petals. Size — large. Average length 7.7 mm. Average width 4.4 mm. Shape — triangular, apex rounded.

Margin — entire. Surface — upper surface glabrous, lower surface pubescent. Color — upper surface varies from 2.5GY 6/6 to 5GY 5/6. Lower surface varies from 7.5R 3/4 to 7.5R 2/6.

*Stamens.*—Average number per flower 45, varies from 42 to 48. Average filament length 15.5 mm. Filament color varies from N9.5/(white) to 5RP 7/6. Anther color varies from 7.5R 4/10 to 7.5R 3/10.

*Pollen.*—Self-fertile. Color varies from 5Y 8.5/8 to 5Y 8/10.

*Pistil.*—Number — normally 1. Surface pubescent. Average length 17.0 mm. Position of the stigma, even with the anthers. Color varies from 2.5GY 8/6 to 5GY 9/4.

*Fragrance.*—Heavy, varies with age of flower.

*Color.*—Varies from 5RP 8/6 to 7.5RP 9/2.

*Number flowers per flower bud.*—Usually one.

*Pedicel.*—Average length 3.9 mm. Average width 1.2 mm. Color varies from 5GY 6/6 to 5GY 5/10.

Fruit:

*Maturity when described.*—Firm ripe.

*Date of first picking.*—Aug. 2, 2008.

*Date of last picking.*—Aug. 8, 2008, varies slightly with climatic conditions.

*Size.*—Medium to large. Average diameter axially 42.8 mm. Average transversely in suture plane 75.3 mm. Average weight 173.2 grams, varies slightly with fertility of the soil, amount of thinning and climatic conditions.

*Form.*—Peento shape.

*Suture.*—Distinct, extends from base to apex.

*Ventral surface.*—Slightly lipped, well sealed.

*Apex.*—Retuse.

*Base.*—Retuse.

Stem:

*Size.*—Small to medium. Average length 7.8 mm. Average diameter 2.9 mm.

*Color.*—Varies from 2.5GY 6/6 to 5GY 5/6.

*Cavity.*—Rounded to slightly elongated in suture plane. Average depth 11.7 mm. Average diameter 29.6 mm.

Flesh:

*Ripens.*—Evenly.

*Texture.*—Firm, meaty.

*Fibers.*—Few, small, tender.

*Firmness.*—Firm.

*Aroma.*—Slight to moderate.

*Amydgalin.*—Undetected.

*Eating quality.*—Very good.

*Flavor.*—Very good, mild, sweet sub-acid.

*Juice.*—Moderate amount, enhances flavor.

*Brix.*—Average Brix 13.8°, varies slightly with amount of fruit per tree and climatic conditions.

*Color.*—Varies from 5Y 9/2 to 5Y 8.5/2.

*Pit cavity.*—Average length 21.8 mm. Average width 27.7 mm. Average depth 12.9 mm. Slight bleeding around pit cavity. Color varies from 5R 3/8 to 5R 2/8.

Skin:

*Thickness.*—Medium.

*Surface.*—Smooth.

*Pubescence.*—Moderate amount, short in length.

*Tendency to crack.*—Very slight.

*Color.*—Ground color varies from 7.5Y 8.5/6 to 7.5Y 8/6. Overspread with 5R 5/10 to 7.5R 4/12 on approximately 75% of surface.

*Tenacity.*—Tenacious to flesh.

*Astringency.*—None.

Stone:

*Type.*—Clingstone.

*Size.*—Medium. Average length 19.2 mm. Average width 26.8 mm. Average thickness 24.8 mm.

*Form.*—Peento shape, resembling shape of fruit.

*Base.*—Flat to slightly retuse.

*Apex.*—Flat, some stones slightly rounded.

*Surface.*—Irregularly furrowed toward apex, pitted toward base. Pits vary from round to elongated.

*Sides.*—Unequal, one side extending outward further from suture plane.

*Ridges.*—Small, narrow ridges extending from base toward apex.

*Tendency to split.*—Slight.

*Color.*—Varies from 10R 3/4 to 10R 2/6, when dry.

Kernel:

*Size.*—Small. Average length 7.6 mm. Average width 10.9 mm. Average thickness 9.4 mm.

*Form.*—Ovoid.

*Viability.*—Viable, complete embryo development.

*Skin.*—Color varies from 5Y 9/6 to 5Y 8.5/6.

Use: Dessert.

*Market.*—Local and long distance.

Keep quality: Good, held firm in cold storage 2 weeks at 38° to 42° F. without internal breakdown or appreciable loss of flavor.

Shipping quality: Good, minimal skin scarring or bruising of flesh during handling and packing trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree (*Prunus persica*), substantially as illustrated and described.

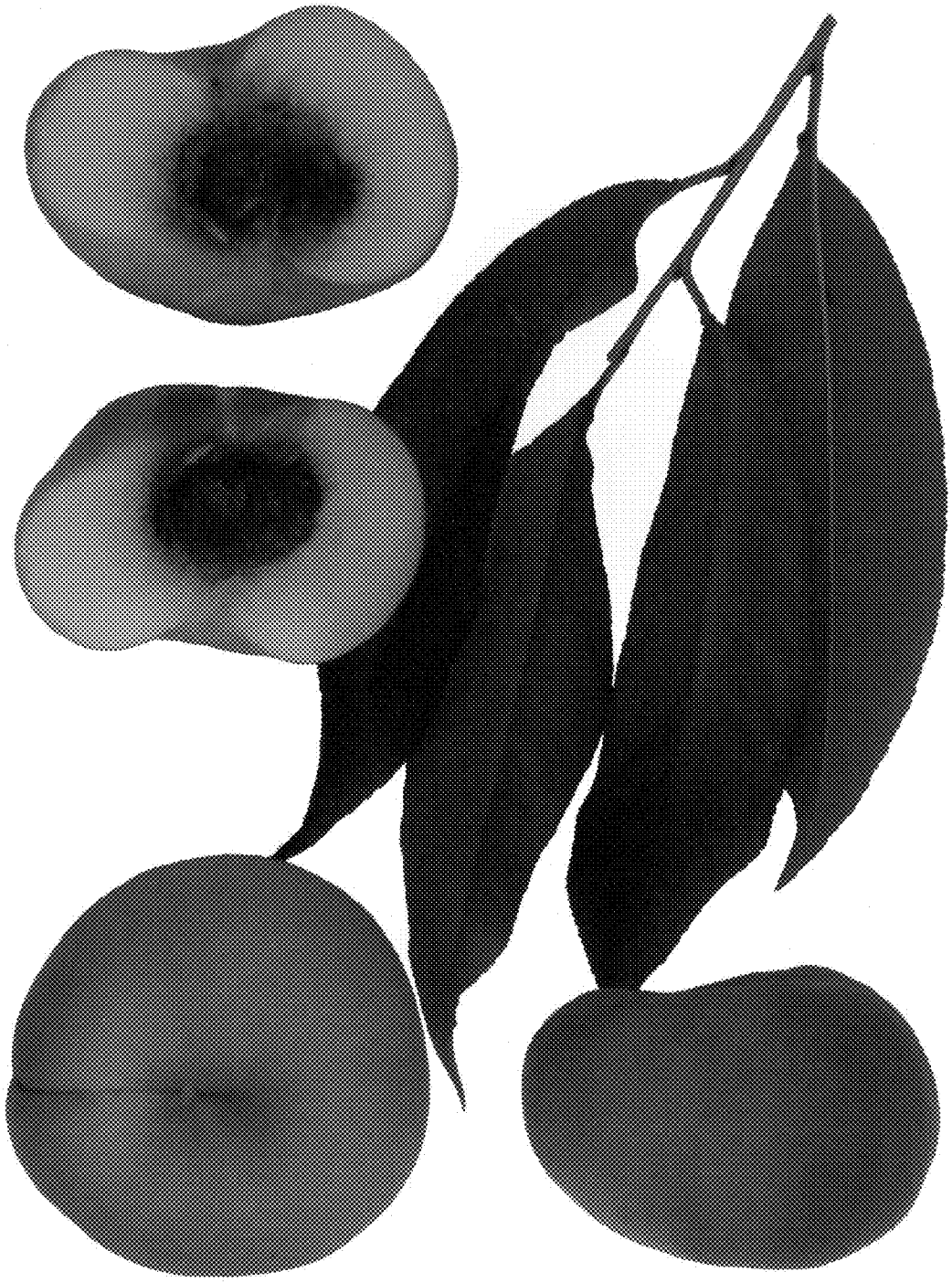

* * * * *